United States Patent [19]

Dokunikhin et al.

[11] 4,166,181
[45] Aug. 28, 1979

[54] N,N'-DIPHENYLDIIMIDES OF 6,12, DIALKYL-3,4,9,10-ANTHANTHRENE-TETRACARBOXYLIC ACID

[76] Inventors: Nikolai S. Dokunikhin, Presnensky val, 42, kv. 23; Georgy N. Vorozhtsov, Sadovo-Spasskaya ulitsa, 21, kv. 268; Faina I. Kichina, Trubnikovsky pereulok, 34, kv. 2; Nikolai B. Feldbljum, Bolshoi Golovin pereulok, 12, kv. 10, all of Moscow, U.S.S.R.

[21] Appl. No.: 841,825

[22] Filed: Oct. 6, 1977

Related U.S. Application Data

[63] Continuation of Ser. No. 689,053, May 24, 1976, abandoned, which is a continuation of Ser. No. 550,654, Feb. 18, 1975, abandoned, which is a continuation of Ser. No. 348,629, Apr. 6, 1973, abandoned.

[51] Int. Cl.² .................. C07D 471/06; C07D 493/06; C07D 519/00
[52] U.S. Cl. .................................... 546/31; 260/345.3; 260/590 FB; 546/52; 568/808; 585/26
[58] Field of Search ...................... 260/281 P; 546/31

[56] References Cited

FOREIGN PATENT DOCUMENTS 1385596 7/1975 United Kingdom ................. 260/281 P

OTHER PUBLICATIONS

Doukunikhin et al. Chem Abs. 82, 113191z (1974).

Primary Examiner—Mark L. Berch
Attorney, Agent, or Firm—Holman & Stern

[57] ABSTRACT

Novel anthanthrene derivatives characterized by the general formula

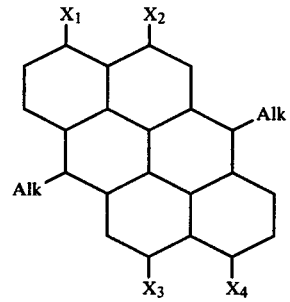

where Alk is an alkyl $C_1$–$C_{10}$, $X_1$, $X_2$ and $X_3$, $X_4$ stand for a group (1) —$CH_2$—$CH_2$— or a group

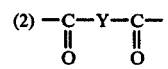

wherein Y is an oxygen atom or an imino-group, either unsubstituted or containing substituents: alkyl, cycloalkyl, aryl; or, else, one of $X_1$ and $X_2$, as well as one of $X_3$ and $X_4$ is a CO-group, the other X then entering, corresponding, into the benzimidazole cycle. The structure of said compounds can be either symmetrical or non-symmetrical with respect to $X_1$, $X_2$ and $X_3$, $X_4$.

Said anthanthrene derivatives are produced by cyclization in the presence of condensing agents of compounds having the formula

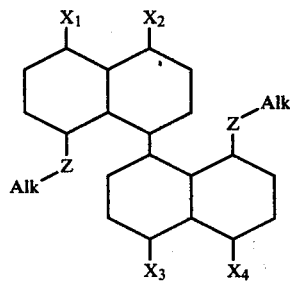

where Z is either CHOH or CO, and Alk, $X_1$, $X_2$, $X_3$ and $X_4$ are as defined above.

Some of the said anthanthrene derivatives are used as dyes or pigments, while others serve as starting products for producing dyes or pigments.

1 Claim, No Drawings

N,N'-DIPHENYLDIIMIDES OF 6,12, DIALKYL-3,4,9,10-ANTHANTHRENE-TETRACARBOXYLIC ACID

This is a continuation of application Ser. No. 689,053, filed May 24, 1976 abandoned which in turn is continuation of Ser. No. 550,654 filed Feb. 18, 1975, abandoned which is a continuation of Ser. No. 348,629 filed Apr. 6, 1973, which is now abandoned.

BACKGROUND AND SUMMARY OF THE INVENTION

The present invention relates to anthanthrene derivatives and to a method of producing such derivatives. The anthanthrene derivatives proposed herein have the general formula (I):

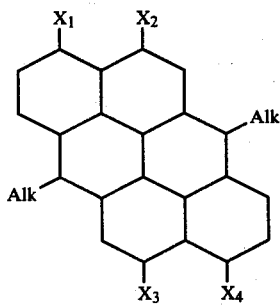

wherein Alk is an alkyl $C_1$–$C_{10}$, $X_1$, $X_2$ and $X_3$, $X_4$ stand for a group (1) —$CH_2$—$CH_2$—; or a group

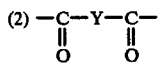

where Y is an oxygen atom, an imino-group, either unsubstituted or containing substituents: alkyl, cycloalkyl, aryl; (3) or, else, one of $X_1$ and $X_2$ and one of $X_3$ and $X_4$ is a CO-group, and then the other X is, correspondingly, in the benzimidazole cycle; the compounds of said formula (I) having their structure either symmetrical or non-symmetrical with respect to $X_1$, $X_2$, and $X_3$, $X_4$.

Some of said derivatives can be used as intermediates for producing dyes and pigments, others, as dyes and the pigments. These derivatives are novel compounds and are not described in literature.

The object of the present invention is to provide the synthesis of novel dyes and pigments, as well as of intermediates for producing dyes and pigments.

Said object is accomplished by the provision of a method which, according to the invention, resides in cyclization of compounds of the general formula (II):

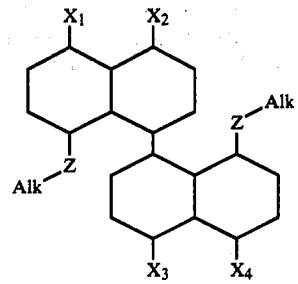

where Z is —COOH, —CO— and $X_1$, $X_2$, $X_3$, $X_4$ are as defined above, in the presence of condensing agents.

For the realization of the present method, compounds of formula II are combined in the presence of condensing agents. The resulting compound of formula I is separated by filtering the reaction mass (if necessary, the reaction mass may be diluted with water prior to filtering). As an example of condensing agents, phosphorus oxychloride, phosphoric acid, a mixture of alcohol and hydrogen chloride, sulphuric acid, a mixture of acetic and hydrobromic acid, sodium hydroxide and potassium hydroxide may be cited.

The process of cyclization of the compounds of the general formula II can be carried out in the presence of reducing agents. In this case the yield will be enhanced.

The starting compounds of the general formula (II) where $X_1$, $X_2$ and $X_3$, $X_4$ are a —$CH_2$—$CH_2$— group, are prepared as follows. 5-Acyl-6-aminoacenaphthene is diazotized with sodium nitride, and the resulting diazo-compound is treated with an ammonia solution of cuprous oxide, giving 5,5'-diacenaphthenyl-6,6'-diacyl.

The starting compounds of the general formula (II) where $X_1$, $X_2$ and $X_3$, $X_4$ are a

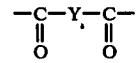

with Y standing for an oxygen atom, are prepared through oxidation of 5,5'-diacenaphthenyl-6,6'-diacyl with compounds of hexavalent chromium in an acidic medium. The resulting compound is the anhydride of 1,1'-dinaphthyl-8,8'-diacyl-4,4',5,5'-tetracarboxylic acid.

The starting compounds of the general formula (II) where $X_1$, $X_2$ and $X_3$, $X_4$ represent a group

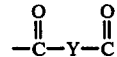

with Y standing for a substituted or unsubstituted imino-group, are produced by reacting an amine or ammonia with the anhydride of 1,1'-dinaphthyl-8,8'-diacyl-4,4',5,5'-tetracarboxylic acid. As an amine use may be made of aliphatic, cycloaliphatic, aromatic amines, diamines, for example, orthophenylenediamine.

Compounds of the general formula (I) wherein $X_1$, $X_2$ and $X_3$, $X_4$ are a

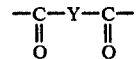

group and Y is a substituted imino-group can also be prepared through condensation of 6,12-dialkyl-3,4,9,10-anthanthrenetetracarboxylic acid anhydride with corresponding amines. The reaction may be carried out with adding condensing and dehydrating agents. The reaction can be run in a solvent. The above-stated can be illustrated by the following diagram:
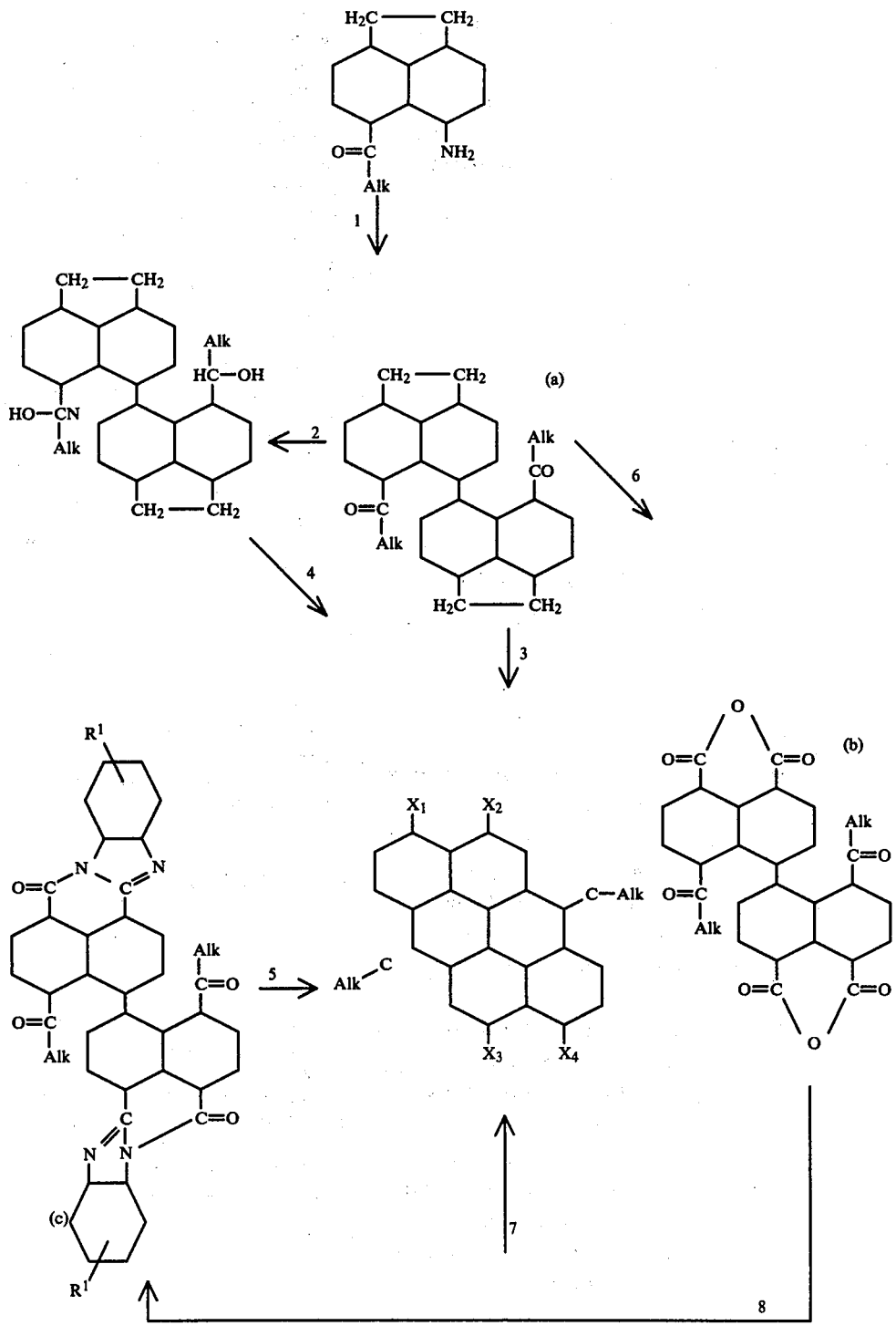

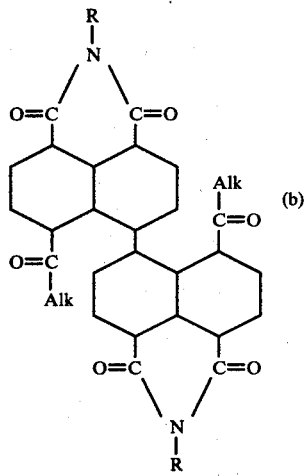

where Alk is an alkyl $C_1$–$C_{10}$, R is H, an alkyl, cycloalkyl, substituted or unsubstituted aryl. R may be either the same, or different. R' is an alkoxy, halogen, etc.

The compounds of formula (I) where $X_1$, $X_2$ and $X_3$, $X_4$ are a —$CH_2$—$CH_2$— group, as well as where $X_1$, $X_2$ and $X_3$, $X_4$ are a

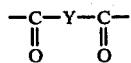

group, wherein Y is an oxygen atom, are intermediates for producing valuable pigments and dyes.

The compounds of formula (I) where $X_1$, $X_2$ and $X_3$, $X_4$ are a

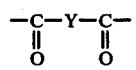

group wherein Y is an imino-group, either unsubstituted or containing substituents, are valuable dyes and pigments with a colour ranging from red to violet. They are noted for the brightness of hue and high fastness, especially to light. The pigments feature good hiding power. Pigments of cherry colour are of special interest in view of scarcity of dyes and pigments having such a hue.

Some of the pigments are noted for their polymorphism, so that pigments with different hues can be obtained from the same chemical substance.

The compounds of formula (I) where $X_1$, $X_2$ and $X_3$, $X_4$ are a

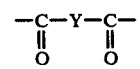

group wherein Y is an oxygen atom can be used for producing heat-resistant polymer materials.

DESCRIPTION OF THE PREFERRED EMBODIMENTS

For a better understanding of the invention, the following illustrative examples are given hereinbelow.

EXAMPLE 1

Producing of 6,12-dime/thyl-3,4,9,10-diaceanthanthrene (a) In a mixture of phosphorus oxychloride and concentrated phosphoric acid.

1 g of 5,5'-diacenaphthenyl-6,6'-diacetyl is suspended in 30 ml of concentrated phosphoric acid and then 6 ml of phosphorus oxychloride are added thereto. The mixture is kept at room temperature for 1.5 hours. After that the reaction mass is poured into 150 ml of water, the precipitate is filtered off, washed to neutral reaction, and dried. The dried precipitate weighs 0.92 g. It is treated with boiling dioxane, and the portion thereof soluble in boiling dioxane is separated, its weight being 0.22 g. The yield is 24%. The substance has the form of greenish-brown prisms (from dioxane) and does not melt till 360° C. Found, %: C, 94.41 94.47; H, 5.46 5.41 Molecular weight, 356 (as determined mass spectrometrically) $C_{18}H_{20}$ Calculated: C, 94.88 H, 5.12 molecular weight, 356.44.

(b) In a mixture of acetic and hydrobromic acid.

1 g of 5,5'-diacenaphthenyl-6,6'-diacetyl is dissolved under heating in 50 ml of glacial acetic acid, and 20 ml of concentrated hydrobromic acid are added thereto. A precipitate gradually falls out. The keeping time at a boiling point is 1 hour. After the cooling the precipitate is filtered off, washed with water to neutral reaction and dried. 0.85 g of a dark-green product are obtained. The product is treated with boiling dioxane, and the portion soluble in boiling dioxane is separated. The weight of the crystalline product separated from dioxane is 0.15 g. The yield is 17%. The identity of the product with that obtained by the procedure described in (a) is confirmed by the coincidence of their respective IR-spectra.

(c) In concentrated sulphuric acid.

1 g of 5,5'-diacenaphthyl-6,6'-diacetyl is dissolved in 10 ml of concentrated sulphuric acid. The solution of a bright yellow colour is heated to 60° C. After keeping the reaction mass at this temperature for 2 hours, it is poured onto a mixture of water and ice. The dark green precipitate is filtered off, washed with water to neutral reaction and dried. The weight thereof is 0.9 g. This product is treated with boiling dioxane. The portion soluble in boiling dioxane is separated. The weight of the crystalline product separated from dioxane is 0.12 g. The yield is 13%. The identity of the product thus obtained with that obtained by the procedure described in (a) is confirmed by the coincidence of their respective IR-spectra.

(d) In an alcoholic solution of HCl.

0.5 g of 5,5'-diacenaphthenyl-6,6'-diacetyl in 70 ml of a 5% solution of HCl in ethanol is boiled for 3 hours. The precipitate is filtered off, washed with alcohol and dried. 0.3 g of 6,12-dimethyl-3,4,9,10-diaceanthanthrene is obtained, the yield being 66% of the theoretical amount. The product is crystallized from benzene. The identity of the product thus obtained with that obtained by the procedure described in (a) is confirmed by the coincidence of their respective IR-spectra.

(e) 2.0 g of 5,5'-diacenaphthenyl-6,6'-diacetyl and 5 g of zinc dust in 30 ml of a 4% solution of HCl in ethanol are boiled during 2 hours. The precipitate is filtered off, dried and extracted with benzene. 0.8 g of 6,12-dimethyl-3,4,9,10-diaceanthanthrene is obtained. The product does not melt till 360° C. The yield is 44%. The identity of the product with that obtained by the procedure described in (a) is confirmed by the coincidence of their respective IR-spectra.

(f) 0.1 g of 5,5'-diacenaphthenyl-6,6'-diacetyl and 8.5 g of $SnCl_2.2H_2O$ in 70 ml of a 4% solution of HCl in ethanol are boiled during 3 hours. The precipitate is filtered off, washed with alcohol and benzene, and dried. 0.9 g of 6,12-dimethyl-3,4,9,10-diaceanthanthrene is obtained. The yield is 98%. The identity of the product with that obtained by the procedure described in (a) is confirmed by the coincidence of their respective IR-spectra.

(g) 2.0 g of 5,5'-diacenaphthenyl-6,6'-diacetyl and 4.0 g of zinc dust are heated in a mixture of 75 ml of acetic acid and 10 ml of a 4% solution of HCl in ethanol at 90° C. during 3 hours. The precipitate is filtered off, washed with alcohol and dried. 1.2 g of 6,12-dimethyl-3,4,9,10-diaceanthanthrene are obtained. The yield is 66%. The identity of the product with that obtained by the procedure described in (a) is confirmed by the coincidence of their respective IR-spectra.

(h) 1.0 g of 5,5'-diacenaphthenyl-6,6'-di-(α-oxyethyl) is stirred in 20 ml of concentrated sulphuric acid at a temperature of 20 to 25° C. during 15 minutes. The reaction mass is poured onto 100 ml of water, the precipitate is filtered off, washed to neutral reaction and dried. Its weight is 0.9 g. The portion soluble in boiling dioxane is separated (0.3g). The yield is 33%, the product being greenish-brown prisms (from dioxane), which does not melt till 360° C. The identity of this product with that obtained by the procedure described in (a) is confirmed by the coincidence of their respective IR-spectra.

(i) 1.0 g of 5,5'-diacenaphthenyl-6,6'-di-(α-oxyethyl) is dissolved in 50 ml of acetic acid, 2 ml of hydrobromic acid are added thereto, the resulting solution is heated to 60° C. and kept at this temperature for 5 minutes. The orange precipitate is filtered, washed with acetic acid and water, and dried. The yield of the product is 55%, its weight is 0.5 g. The greenish-brown prisms (from dioxane) do not melt till 360° C. The identity of the product with that obtained by the procedure described in (a) is confirmed by the coincidence of their respective IR-spectra.

(j) 1.0 g of 5,5'-diacenaphthenyl-6,6'-di-(α-oxyethyl) is dissolved in 90 ml of a 5% solution of HCl in ethanol and boiled during 1.5 hours. The orange precipitate is filtered off, washed with alcohol and dried. The weight of the product is 0.5 g, the yield is 55%. Greenish-brown prisms (from dioxane). The product does not melt till 360° C. The identity of the product with that obtained by the procedure described in (a) is confirmed by the coincidence of their respective IR-spectra.

(k) 1.0 g of 5,5'-diacenaphthenyl-6,6'-diacetyl and 1.0 g of $SnCl_2.2H_2O$ are heated in a mixture of 30 ml of acetic acid and 1.5 ml of hydrobromic acid at 90 to 95° C. during 2 hours. The precipitate is filtered off, washed with water and dried. 0.9 g of 6,12-dimethyl-3,4,9,10-diaceanthanthrene is obtained. The yield is 98.5%. Greenish-brown prisms (from dioxane), the product does not melt till 360° C. The identity of the product with that obtained by the procedure described in (a) is confirmed by the coincidence of their respective IR-spectra.

(l) 1.0 g of 5,5'-diacenaphthenyl-6,6'-diacetyl and 2.0 g of KOH are boiled in 20 ml of pyridine for 30 minutes. The reaction mass is poured onto 100 ml of water, the precipitate is filtered off, washed with water and dried. 0.9 g of the product is obtained which is treated with boiling dioxane, and the portion soluble in the boiling dioxane is separated. The weight of the crystalline product isolated from the dioxane is 0.8 g. The yield is 88%. The identity of the product thus obtained with that prepared in (a) is confirmed by the coincidence of their respective IR-spectra.

EXAMPLE 2

Producing of 6,12-diethyl-3,4,9,10-diaceanthanthrene (a) 1.0 g of 5,5'-diacenaphthenyl-6,6'-dipropionyl is heated in a mixture of 60 ml of acetic acid and 10 ml of hydrobromic acid at a temperature of 70° C. during 2 hours. The dark green precipitate is filtered off, washed with a small quantity of acetic acid, then with water, and dried. 0.5 g of the product is obtained, the yield being 50%. The product is recrystallized from a benzene/petroleum ether mixture; the product does not melt till 250° C.

Found, %: C, 93.19, 93.32; H, 6.22, 6.48.

Calctd; $C_{30}H_{24}$ C, 93.71; H, 6.29.

(b) 2.0 g of 5,5'-diacenaphthenyl-6,6'-dipropionyl and 4.0 g of zinc dust are heated in a mixture of 75 ml of acetic acid and 10 ml of a 4% solution of HCl in ethanol at 90° C. during 3 hours. The precipitate is filtered off, washed with alcohol and dried. 1.3 g of the product are obtained, the yield being 70%. After recrystallization from a benzene/petroleum ether mixture, the IR-spectrum of the product coincides with the IR-spectrum of the substance produced above.

EXAMPLE 3

Producing of 6,12-dimethyl-3,4,9,10-anthanthrene-tetracarboxylic acid anhydride (a) 2.0 g of 1,1'-dinaphthyl-8,8'-diacetyl-4,4',5,5'-tetracarboxylic acid anhydride are dissolved in 50 ml of phosphoric acid and 6 ml of phosphorus oxychloride are added to the solution. The reaction mass is heated to 145° C. A red-violet precipitate falls out. The reaction mass is cooled and then poured onto 250 g of a mixture of ice and water. The precipitate is filtered off, washed with water to neutral reaction and dried.

1.6 g of a substance are obtained in the form of dark violet prisms (from nitrobenzene), which do not melt till 360° C. The yield is 86%.

Found, %: C, 74.64 75.54 H, 2.3 2.2 Molecular weight is 444 (as determined mass spectrometrically) Calctd $C_{18}H_{12}O_6$ C, 75.71 H, 2.73 Molecular weight, 444.38.

(b) 25.0 g of 1,1'-dinaphthyl-8,8'-diacetyl-4,4',5,5'-tetracarboxylic acid anhydride are dissolved in 500 ml of 75% sulphuric acid. Then the solution is heated to 70° C. and stirred at this temperature during 10 hours. The reaction mass is cooled, the precipitate is filtered off through a glass porous filter, is washed with a small quantity of 75% sulphuric acid, then with water to neutral reaction, and dried. 18 g of 6,12-dimethyl-3,4,9,10-anthanthrenetetracarboxylic acid anhydride are thus obtained. The yield is 75%. The IR-spectrum of the product after recrystallization thereof from nitrobenzene coincides with the IR-spectrum of the sample produced above.

(c) 5.0 g of 1,1'-dinaphthyl-8,8'-diacetyl-4,4',5,5'-tetracarboxylic acid anhydride in 85 ml of 80% sulphuric acid are heated to 70° C., and, with 5.0 g of zinc dust being gradually added thereto, are stirred during 6 hours. The reaction mass is then cooled, the precipitate is filtered off, washed with a small quantity of 80% sulphuric acid and with water to neutral reaction. After that the precipitate is dissolved in 150 ml of a 5% solution of soda, filtered, the filtrate is acidulated with hydrochloric acid for the reaction to Congo to be acidic, the resulting precipitate is filtered off, washed with water to neutral reaction and dried. The yield of the product is 4.0 g (86%).

(d) 1.0 g of 1,1'-dinaphthyl-8,8'-diacetyl-4,4',5,5'-tetracarboxylic acid and 1.5 g of sodium hydrosulphite in 40 ml of a 10% solution of KOH are heated to 95° C. during 1 hour. The precipitated salt of 6,12-dimethyl-3,4,9,10-anthanthrenetetracarboxylic acid is filtered off, transferred into 30 ml of 10% HCl, heated to 90° C., then cooled down, the resulting precipitate is filtered off, washed with water and dried. 0.72 g of 6,12-dimethyl-3,4,9,10-anthanthrenetetracarboxylic acid dianhydride is thus obtained. The yield is 84%, the IR-spectrum of the product coincides with the IR-spectrum of the specimen obtained as described in (a).

(e) 1.0 g of 1,1'-dinaphthyl-8,8'-diacetyl-4,4',5,5'-tetracarboxylic acid and 1.0 g of sodium hydrosulphite in 40 ml of a 5% solution of NaOH are heated to 95° C. during 2 hours. The precipitated salt of 6,12-dimethyl-3,4,9,10-anthanthrenetetracarboxylic acid is filtered off and transferred into 30 ml of 10% HCl, is heated to 90° C. and then cooled down. The resulting precipitate is filtered off, washed with water and dried. 0.82 g of 6,12-dimethyl-3,4,9,10-anthanthrenetetracarboxylic acid dianhydride is thus obtained. The yield is 95%. The IR-spectrum of the product coincides with the IR-spectrum of the specimen produced as described in (a).

EXAMPLE 4

Producing of N,N-diphenyldiimide of 6,12-dimethyl-3,4,9,10-anthanthrenetetracarboxylic acid 0.5 g of N,N-diphenyldiimide of 1,1'-dinaphthyl-8,8'-diacetyl-4,4',5,5'-tetracarboxylic acid is heated in a mixture of 15 ml of phosphoric acid and 3 ml of phosphorus oxychloride during 1 hour at 145° C. The crystalline red-violet precipitate is filtered off, washed first with water to neutral reaction, then with ethanol, and dried.

0.41 g of a substance is obtained in the form of red-violet needles (from aniline); the product does not melt till 360° C. The yield is 78%.

Found, %: C, 80.06, 79.72; H, 3.63, 3.80; N, 4.43, 4.40.

Calctd, %: $C_{40}H_{22}N_2O_4$ C, 80.8; H, 3.73; N, 4.72.

The substance dyes polymer materials in bulk, for example, polyvinyl chloride, oil coatings, nitrocellulose lacquers, alkyd cold- and hot-drying varnishes into red-violet and violet colours, depending on the crystalline modification. The light fastness is 8 points in case of full tone and 7 to 8 points in case of a 1:10 diluting ratio. Similarly, substituted N,N-diphenyldiimides of 1,1'-dinaphthyl-8,8'-diacetyl-4,4',5,5'-tetracarboxylic acid, e.g., containing a haloid, an alkoxy group, etc. in the benzene cycle, form compounds of formula (I), which dye polymer materials in bulk, for example, polyvinyl chloride, oil coatings, nitrocellulose lacquers, alkyd cold- and hot-drying varnishes, and other coatings, into red, red-violet and violet colours with high colouristic characteristics.

EXAMPLE 5

Preparing of diimidazole of 6,12-dimethyl-3,4,9,10-anthanthrenetetracarboxylic acid Under the conditions similar to those of Example 3 (b), from 5.0 g of the product of condensation of 1,1'-dinaphthyl-8,8'-diacetyl-4,4',5,5'-tetracarboxylic acid anhydride with ortho-phenylenediamine 4.0 g of diimidazole of 6,12-dimethyl-3,4,9,10-anthanthrenetetracarboxylic acid are obtained. The product is of dark blue colour. The yield is 85%.

The product dyes polymer materials in bulk, for example, polyvinyl chloride, oil coatings, nitrocellulose lacquers, alkyd cold- and hot-drying varnishes and other coatings into blue colour with high colouristic characteristics.

Similarly, products of condensation of 1,1'-dinaphthyl-8,8'-diacetyl-4,4',5,5'-tetracarboxylic acid anhydride with a substituted ortho-phenylenediamine (the substituents being a haloid, an alkoxy, etc.) form compounds of formula (I), which dye polyvinyl chloride in bulk, oil coatings, nitrocellulose lacquers, and alkyd varnishes into blue colours of various hues with high colouristic characteristics.

What is claimed is:

1. Anthanthrene compounds of the formula:

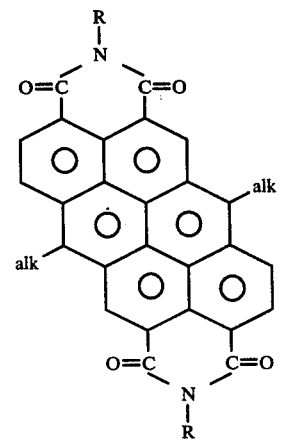

wherein alk is an alkyl group having $C_2$–$C_{10}$ carbon atoms, and R is selected from the group consisting of phenyl, monohalophenyl and monoalkoxyphenyl.

* * * * *